United States Patent [19]  [11] 4,025,629
Coverdale [45] May 24, 1977

[54] P-(TRIFLUOROMETHYL-QUINOLYLAMINO)BENZAMIDES, PHARMACEUTICAL DOSAGE FORMS AND METHOD OF TREATMENT

[75] Inventor: Charles E. Coverdale, Portage, Mich.

[73] Assignee: The Upjohn Company, Kalamazoo, Mich.

[22] Filed: Mar. 21, 1975

[21] Appl. No.: 560,918

Related U.S. Application Data

[63] Continuation-in-part of Ser. No. 431,252, Jan. 7, 1974, abandoned, which is a continuation of Ser. No. 227,608, Feb. 18, 1972, abandoned, which is a continuation-in-part of Ser. No. 848,739, Aug. 8, 1969, abandoned.

[52] U.S. Cl. .................... 424/250; 260/287 AR; 424/258; 260/268 BQ
[51] Int. Cl.² ............... A61K 31/47; C07D 215/44
[58] Field of Search ............ 260/268 BQ; 424/250

[56] References Cited

UNITED STATES PATENTS 2,940,974   6/1960   Surrey .................. 260/268 BQ
3,632,761   1/1972   Graham et al. ......... 260/268 BQ

OTHER PUBLICATIONS

Fukami, *Amides of 4–Quinolylamino Acid as Chemotherapeutic Agents*, Thesis, (1967), p. 8.

*Primary Examiner*—Paul M. Coughlan, Jr.
*Attorney, Agent, or Firm*—John J. Killinger; Roman Saliwanchik

[57] ABSTRACT

Novel p-(trifluoromethylquinolylamino)benzamides are provided, for example, p-[(7-trifluoromethyl-4-quinolyl)-amino]-N,N-(3-methyl-3-azapentamethylene)benzamide and 1-[p-[[7-(trifluoromethyl)-4-quinolyl]amino]benzoyl]piperazine dihydrochloride. Also provided are pharmaceutical dosage unit forms for systemic administration and methods for their systemic administration. The compound, dosage unit forms and methods of systemic administration are useful in obtaining antihypertensive and anti-anxiety effects in mammals.

6 Claims, No Drawings

P-(TRIFLUOROMETHYLQUINOLYLAMINO)BENZAMIDES, PHARMACEUTICAL DOSAGE FORMS AND METHOD OF TREATMENT

CROSS REFERENCES TO RELATED APPLICATIONS

This application is a continuation-in-part of application Ser. No. 431,252, filed Jan. 7, 1974, now ahandoned, which in turn is a continuation of application 227,608, filed Feb. 18, 1972, now abandoned, which in turn is a continuation-in-part of application Ser. No. 848,739, filed Aug. 8, 1969, now abandoned.

The Ph.D. thesis of M. H. Fukami, referred to hereafter, appears as a reference in the file of U.S. Pat. No. 3,632,761, issued Jan. 4, 1972.

BACKGROUND OF THE INVENTION

Compounds of the general Formula I, infra, wherein $R_3$ is hydrogen are prepared by methods available in the chemical literature (e.g., methods described in the references given below) to couple p-aminobenzamides with a 4-chloroquinoline in a lower alkanol such as ethanol using as catalyst one equivalent of hydrochloric acid. The p-aminobenzamides are derived from the corresponding p-nitrobenzamides by catalytic hydrogenation; the p-nitrobenzamides being prepared from the corresponding amines or ammonia and p-nitrobenzoyl chloride.

Compounds of the general Formula I, infra, wherein $R_3$ is alkyl are prepared by treating a compound wherein $R_3$ is hydrogen with the corresponding alkyl halide, e.g., methyl iodide or bromide and an alkali metal halide or alkali metal amide, e.g., sodium hydride or sodium amide.

M. H. Fukami, Amides of 4-Quinolylaminoacids as Chemotherapeutic Agents, University of Michigan, Ph.D. Thesis 1967, describes 1-[p-[(7-chloro-4-quinolyl)amino]-N,N-(3-methyl-3-azapentamethylene]benzamide and its meta isomer. Slight activity against *Schistosoma Mansoni* cercariae in mice and against *Plasmodium berghei* at a dose of 160 mg./kg. subcutaneously to mice are disclosed.

SUMMARY OF THE INVENTION

This invention relates to p-(trifluoromethylquinolylamino)benzamides represented by the structural formula:

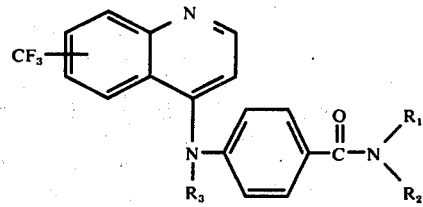

I wherein $R_1$ is hydrogen or alkyl having 1 to 4 carbon atoms, inclusive; $R_2$ is hydrogen or alkyl having 1 to 4 carbon atoms, inclusive; $R_1$ and $R_2$ when taken together with

is selected from the group consisting of unsubstituted and mono-alkyl and polyalkyl substituted pyrrolidino, piperidino, hexamethylenimino, morpholino, piperazino, and 4-benzylpiperazino; and $R_3$ is hydrogen or alkyl having 1 to 4 carbon atoms, inclusive; and the acid addition salts thereof.

It also relates to the pharmaceutical dosage unit forms adapted for systemic administration to obtain antihypertensive and anti-anxiety effects consisting essentially of an effective nontoxic amount of a compound according to Formula I. Further the invention relates to methods of obtaining antihypertensive and anti-anxiety effects in mammals, for example humans and valuable warm-blooded animals such as dogs, cats, and other domestic animals by administering systemically to the mammals the aforesaid pharmaceutical dosage unit forms supplying an effective nontoxic amount for antihypertensive and anti-anxiety effects.

Examples of halogen are fluorine, chlorine, and bromine. Examples of alkyl having from 1 to 4 carbon atoms, inclusive, are methyl, ethyl, propyl, butyl and isomeric forms thereof. Examples of saturated heterocyclic amino radicals constituting $R_1$ and $R_2$ taken together with $-N\subset$, in addition to those already named, are 2,2-dimethylpyrrolidino, 2-ethylpyrrolidino, 2-isopropylpyrrolidino, 2-sec.butylpyrrolidino, 2-methylpiperidino, 3-methylpiperidino, 4-methylpiperidino, 2-butylpiperidino, 3,4-diethylpiperidino, 2-methylhexamethylenimino, 3,6-dimethylhexamethylenimino, 2,2-dibutylhexamethylenimino, 2-ethylmorpholino, 3,3-dimethylmorpholino, 2-ethyl-5-methylmorpholino, 4-methylpiperazino, 2-methyl-4-benzylpiperazino, 4-butylpiperazino and the like.

The p-(trifluoromethylquinolylamino)benzamides of Formula I in which $R_3$ is hydrogen can be prepared by reacting a trifluoromethyl-4-chloroquinoline having the formula:

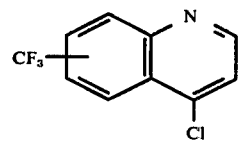

II with a p-aminobenzamide having the formula:

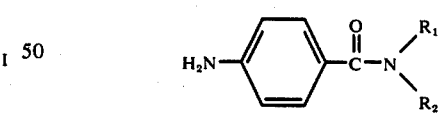

III wherein $R_1$ and $R_2$ are as defined above. The reaction is carried out in accordance with methods known in the art for reacting 4-chloroquinolines with amines, for example, as disclosed in J. Amer. Chem. Soc. 66, 1127 (1944); ibid. 70, 1363 (1948); and J. Chem. Soc. 1014 (1949). Advantageously the Formula II, trifluoromethyl-4-chloroquinoline, and the Formula III, p-aminobenzamide, are reacted in equimolar amounts in the presence of an inert reaction medium, e.g., a lower alkanol such as ethanol, and a catalyst, e.g., an equimolar amount of hydrogen chloride introduced into the reaction mixture in the form of concentrated hydrochloric acid.

The p-(trifluoromethylquinolylamino)benzamides of Formula I in which $R_3$ is alkyl can be prepared by alkylating compounds of Formula I in which $R_3$ is hydrogen. For example, a Formula I compound in which $R_3$ is hydrogen can be treated first with an alkali metal hydride or amide, e.g., sodium amide or sodium hydride, and then with an alkyl halide, the reaction being carried out in the presence of an inert reaction medium, e.g., toluene or xylene.

The trifluoromethyl-4-chloroquinolines of Formula II and the p-aminobenzamides of Formula III, many of which are known, are prepared by known procedures. For example, the trifluoromethyl-4-chloroquinolines can be prepared by the procedure described in J. Amer. Chem. Soc. 69, 371 (1947).

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, and the like. The reaction can be carried out in aqueous or non-aqueous media such as ether, ethyl acetate, and the like.

This invention relates also to pharmaceutical dosage unit forms for systemic administration (oral and parenteral administration) in obtaining unexpectedly advantageous beneficial results in hypertensive and anxiety conditions in mammals including humans and valuable warm-blooded animals such as dogs, cats, and other domestic animals. The term "dosage unit form" as used in this specification and in the claims refers to physically discrete units suitable as unitary dosages for mammalian subjects, each unit containing a predetermined quantity of the essential active ingredient calculated to produce the desired effect in combination with the required pharmaceutical means which adapt the said ingredient for systemic administration. The specification for the novel dosage unit forms of this invention are dictated by and directly dependent on the unique characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules both hard and soft are formulated with suitable diluents and excipients, for example, edible oils, talc, calcium carbonate and the like and also calcium stearate. Liquid preparations for oral administration are prepared in water or aqueous solutions which advantageously contain suspending agents, for example, sodium carboxymethylcellulose, methylcellulose, acacia, polyvinyl pyrrolidine, polyvinyl alcohol and the like. In the case of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 10 to about 1000 mg. of the essential active ingredient per dosage unit form, which as aforesaid may be in the form of a solid oral preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antihypertensive and anti-anxiety effects within the aforesaid effective non-toxic range. Expressed otherwise an amount of the essential active ingredient is provided to a recipient within a range from about 0.1 mg. per kg. to about 15 mg. per kg. of body weight of the recipient.

DESCRIPTION OF THE PREFERRED EMBODIMENTS

The following embodiments illustrate the manner and process of making and using the present invention but are not to be construed as limitations of the inventive concept.

EXAMPLE 1 p-[(7-trifluoromethyl-4-quinolyl)amino]-N,N-(3-methyl-3-azapentamethylene)benzamide A mixture of 6.95 gm. (0.03 mole) of 4-chloro-7-trifluoromethylquinoline [J. Am. Chem. Soc. 69, 371 (1974)] and 6.58 gm. (0.03 mole) of 4-methyl-1-(p-aminobenzoyl)-piperazine [J. Org. Chem. 24, 459 (1959)] in 100 ml. of absolute ethanol and 5.3 ml. of 6N hydrochloric acid is heated at reflux with stirring for 16 hours. The cooled mixture is evaporated, diluted with water, and made alkaline with 40 ml. of 2N sodium hydroxide. The mixture is extracted with chloroform (three 100-ml. portions). The combined extract is washed with water and then with saturated brine, is dried (anhydrous sodium sulfate), and is evaporated. The residue is chromatographed on 1 kg. of silica gel using chloroform-methanol (6:1 by volume). The solid is crystallized from ethanol to yield 7.42 gm. (60% yield) of p-[(7-trifluoromethyl-4-quinolyl)amino]-N,N-(3-methyl-3-azapentamethylene)benzamide, melting point 218.5°–220° C. Concentration of the mother liquor gives an additional 0.9 gm., melting point 218°–220° C.

Analysis: Calc'd. for $C_{22}H_{21}F_3N_4O$: C, 63.76; H, 5.11; F, 13.75; N, 13.52. Found: C, 64.04; H, 5.33; F, 14.39; N, 13.50.

EXAMPLE 2

Other Compounds of Formula I

Following the procedure of Example 1, but replacing 4-methyl-1-(p-aminobenzoyl)piperazine with other p-aminobenzamides of Formula III, there is obtained other p-(trifluoromethylquinolylamino)benzamides of Formula I, such as:

p-[(7-trifluoromethyl-4-quinolyl)amino]-N,N-tetramethylenebenzamide;
p-[(7-trifluoromethyl-4-quinolyl)amino]-N,N-(1,1-dimethyltetramethylene)benzamide;
p-[(7-trifluoromethyl-4-quinolyl)amino]-N,N-(1-isopropyltetramethylene)benzamide;
p-[(7-trifluoromethyl-4-quinolyl)amino]-N,N-(3-methylpentamethylene)benzamide;
p-[(7-trifluoromethyl-4-quinolyl)amino]-N,N-(1-butylpentamethylene)benzamide;
p-[(7-trifluoromethyl-4-quinolyl)amino]-N,N-(2,3-diethylpentamethylene)benzamide;
p-[(7-trifluoromethyl-4-quinolyl)amino]-N,N-(hexamethylene)benzamide;
p-[(7-trifluoromethyl-4-quinolyl)amino]-N,N-(1-methylhexamethylene)benzamide;
p-[(7-trifluoromethyl-4-quinolyl)amino]-N,N-(1-methyl-4-ethyl-3-oxapentamethylene)benzamide;
p-[(7-trifluoromethyl-4-quinolyl)amino]-N,N-(3-butyl-3-azapentamethylene)benzamide;
p-[(7-trifluoromethyl-4-quinolyl)amino]-N,N-(3-benzyl-3-azapentamethylene)benzamide; and
p-[(7-trifluoromethyl-4-quinolyl)amino]-N,N-(3-azapentamethylene)benzamide.

EXAMPLE 3

Other Trifluoromethyl Compound of Formula I

Following the procedures of Examples 1 and 2 but substituting 4-chloro-5-trifluoromethylquinoline, 4-chloro-6-trifluoromethylquinoline, and 4-chloro-8-trifluoromethylquinoline there are obtained the corresponding p-[(5-trifluoromethyl-4-quinolyl)amino]-, p-[(6-trifluoromethyl-4-quinolyl)amino]-, and p-[(8-trifluoromethyl-4-quinolyl)amino]-N,N-(disubstituted)benzamides.

EXAMPLE 4

Hydrochloride Acid Addition Salt 1-(p-Aminobenzoyl)piperidine and 4-chloro-7-trifluoromethylquinoline are reacted in equimolar amounts in hydrochloric acid — acidified ethanol using refluxing conditions. The reaction mixture is evaporated to dryness under reduced pressure and the residue is recrystallized from ethanol to yield p-[(7-trifluoromethyl-4-quinolyl)amino]-N,N-(pentamethylene)benzamide hydrochloride.

Other hydrochlorides are prepared by this procedure wherein the 4-chloro-7-trifluoromethylquinoline is replaced by the other 4-chloro-trifluoromethylquinolines used in Example 3.

EXAMPLE 5 p-[(7-trifluoromethyl-4-quinolyl)amino]-N,N-(3-oxapentamethylene)benzamide Hydrochloride A mixture of 0.1 mole each of 4-(p-aminobenzoyl) morpholine and of 4-chloro-7-trifluoromethylquinoline in 8 ml. of concentrated hydrochloric acid with 500 ml. of absolute ethanol is heated at reflux for 48 hours. The mixture is cooled and filtered to obtain p-[(7-trifluoromethyl-4-quinolyl)amino]-N,N-(3-oxapentamethylene)benzamide hydrochloride.

EXAMPLE 6 p-[(7-trifluoromethyl-4-quinolyl)amino]-N-methylbenzamide hydrochloride

A mixture of 0.1 mole of N-methyl-p-aminobenzamide, 0.1 mole of 4-chloro-7-trifluoromethylquinoline, 10 ml. of concentrated hydrochloric acid and 500 ml. of absolute ethanol is stirred at about 25° C for 30 minutes. A precipitate begins to form, and the mixture is then heated at reflux for 4 hours. The mixture is cooled and filtered to obtain p-[(7-trifluoromethyl-4-quinolyl)amino]-N-methylbenzamide hydrochloride.

Following the same procedure, but substituting p-aminobenzamide for N-methyl-p-aminobenzamide, p-[(7-trifluoromethyl-4-quinolyl)amino]benzamide hydrochloride is obtained.

EXAMPLE 7 p-[(7-trifluoromethyl-4-quinolyl)amino]-N,N-dimethylbenzamide

A mixture of 0.1 mole of N,N-dimethyl-p-aminobenzamide, 0.1 mole of 4-chloro-7-trifluoromethylquinoline, 8 ml. of concentrated hydrochloric acid and 500 ml. of absolute ethanol is heated at reflux for 19 hours, after which 100 ml. of 2.5N sodium hydroxide is added. The mixture is cooled and filtered and the filter cake is recrystallized from methanol. There is thus obtained p-[(7-trifluoromethyl-4-quinolyl)amino]-N,N-dimethylbenzamide.

EXAMPLE 8 p-[(7-trifluoromethyl-4-quinolyl)-N-ethylamino]-N,N-(3-methyl-3-azapentamethylene)benzamide A mixture of 0.01 mole of p-[(7-trifluoromethyl-4-quinolyl)amino]-N,N-(3-methyl-3-azapentamethylene)benzamide. 0.01 mole of sodium hydride (as a 56% suspension in mineral oil) and 150 ml. of toluene is heated at reflux for 30 minutes. Ethyl iodide (3.12 gm.; 0.02 mole) is added to the mixture and refluxing is continued for 3 hours, at which time the mixture is evaporated to dryness under reduced pressure. The residue is extracted with methylene chloride. Evaporation of the extract gives p-[(7-trifluoromethyl-4-quinolyl)-N-ethylamino]-N,N-(3-methyl-3-azapentamethylene)benzamide.

By substituting methyl iodide and butyl iodide, respectively, for ethyl iodide, the corresponding N-methylamino and N-butylamino compounds are obtained.

EXAMPLE 9

1-[p-[[(7-trifluoromethyl)-4-quinolyl]amino]-benzoyl]piperazine dihydrochloride A mixture of 34 g. (0.147 mole) of 4-chloro-7-trifluoromethylquinoline, 30 g. (0.147 mole) of 4-aminobenzoylpiperazine and 14.9 ml. of concentrated hydrochloric acid in 450 ml. of ethanol was stirred at reflux for 2 hours. The resulting suspension was cooled, product collected, and recrystallized from ethanol; yielding 53 g. (76%) of 1-[-[[(7-trifluoromethyl)-4-quinolyl]amino]benzoyl]piperazine dihydrochloride having a m.p. 338°–341° C.

Analysis: Calc'd. for $C_{21}H_{19}F_3N_4O\cdot 2HCl$: C, 53.28; H, 4.47; N, 11.84. Found: C, 52.95; H, 4.57; N, 11.61.

IR: NH/OH 3420 weak; $NH/NH^+/=CH$ 3160; $NH^+$ 2720, 2680, 2600, 2400, 2430; C=O/C=C/NH def 1640 w, 1600 s, 1560, 1535, 1505; $CF_3$/C—N/other 1325, 1290, 1250, 1215, 1165, 1140, 1130, 1120; arom CH/other 825, 750.

In each of Examples 10 through 22, for brevity, p-[(7-trifluoromethyl-4-quinolyl)amino]-N,N-(3-methyl-3-azapentamethylene)benzamide is listed as "essential active ingredient".

EXAMPLE 10

One thousand tablets for oral use, each containing 250 mg. of essential active ingredient are prepared from the following ingredients:

Essential active ingredient — 250 gm.
Dicalcium phosphate — 150 gm.
Methylcellulose, U.S.P. (15 cps) — 6.5 gm.
Talc — 20 gm.
Calcium stearate — 2.5 gm.

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of anxiety in adult humans at a dose of 1 tablet 2 or 3 times a day.

EXAMPLE 11

One thousand two-piece hard gelatin capsules for oral use, each capsule containing 10 mg. of essential active ingredient are prepared from the following ingredients:

Essential active ingredient — 10 gm.
Lactose, U.S.P. — 100 gm.
Starch, U.S.P. — 10 gm.
Talc, U.S.P. — 5 gm.
Calcium stearate —1 gm.

The finely powdered materials are mixed thoroughly, then filled into hard gelatin capsules of appropriate size.

A satisfactory clinical response is obtained in adults showing hypertension with 1 capsule 4 times a day.

EXAMPLE 12

One-piece soft elastic capsules for oral use, each containing 20 mg. of essential active ingredient are prepared in the usual manner by first dispersing the powdered active material in sufficient corn oil to render the material capsulatable.

One capsule 4 times a day is useful in the treatment of moderate hypertension in adult humans.

EXAMPLE 13

An aqueous oral preparation containing in each teaspoonful (5 ml.) 25 mg. of essential active ingredient hydrochloride is prepared from the following ingredients:

Essential active ingredient hydrochloride — 50 gm.
Methylparaben, U.S.P. — 7.5 gm.
Propylparaben, U.S.P. — 2.5 gm.
Saccharin sodium — 12.5 gm.
Cyclamate sodium — 2.5 gm.
Glycerin — 3,000 ml.
Tragacanth powder — 10 gm.
Orange oil flavor — 10 gm.
F.D. and C. Orange dye — 7.5 gm.
Deionized water, q.s. to — 10,000 ml.

The foregoing aqueous preparation is useful in the treatment of adult agitated depression and anxiety at a dose of 1 teaspoonful 4 times a day.

EXAMPLE 14

One thousand tablets for oral administration, each containing 10 mg. of essential active ingredient and 16.2 mg. of phenobarbital are prepared from the following ingredients:

Essential active ingredient, micronized — 10 gm.
Phenobarbital — 16.2 gm.
Lactose — 150 gm.
Starch — 15 gm.
Magnesium stearate — 1.5 gm.

The ingredients are thoroughly mixed and slugged. The slugs are broken down by forcing through a screen and the resulting granules are then compressed into tablets.

These tablets are useful in tranquilizing excited dogs at a dose of 1 to 3 tablets depending on the weight of the animal and its condition.

EXAMPLE 15

A sterile aqueous suspension suitable for intramuscular injection and containing in each milliliter 100 mg. of essential active ingredient is prepared from the following ingredients:

Essential active ingredient — 10 gm.
Polyethylene glycol 4000, U.S.P. — 3 gm.
Sodium chloride — 0.9 gm.
Polysorbate 80, U.S.P. — 0.4 gm.
Sodium metabisulfite — 0.1 gm.
Methylparaben, U.S.P. — 0.18 gm.
Propylparaben, U.S.P. — 0.02 gm.
Water for injection, q.s. to — 100 ml.

The preceding sterile injectable is useful in the treatment of anxiety and apprehension prior to surgery at a dose of 1 or 2 ml.

EXAMPLE 16

One thousand suppositories, each weighing 2.5 gm. and containing 250 mg. of essential active ingredient, are prepared from the following ingredients:

Essential active ingredient — 250 gm.
Propylene glycol — 165 gm.
Polyethylene glycol 4000 q.s. — 2,500 gm.

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of post-surgical anxiety at a dose of 1 suppository rectally twice a day.

EXAMPLE 17

One thousand hard gelatin capsules for oral use, each containing 25 mg. of essential active ingredient and 25 mg. of hydrochlorothiazide are prepared from the following ingredients:

Essential active ingredient, micronized — 25 gm.
Hydrochlorothiazide — 25 gm.

Starch — 125 gm.
Talc — 25 gm.
Magnesium stearate — 1.5 gm.

One capsule 4 times a day is useful in the relief of moderate hypertension in adult humans.

EXAMPLE 18

Ten thousand scored tablets for oral use, each containing 25 mg. of essential active ingredient and 0.08 mg. of reserpine, are prepared from the following ingredients and using the procedure of Example 13.

Essential active ingredient, micronized — 250 mg.
Reserpine — 0.8 gm.
Lactose — 1,500 gm.
Corn starch — 500 gm.
Talc — 500 gm.
Calcium stearate — 25 gm.

This combination of active materials is effective in reducing hypertension in adult humans. The dose is one-half of two tablets 3 times a day, depending on the severity of the condition.

EXAMPLE 19

Aqueous Suspension

An aqueous suspension for oral administration is prepared by suspending the essential active ingredient at a concentration of 10 mg./ml. in an aqueous solution containing 1% of sodium carboxymethylcellulose. This suspension is used for bringing about hypotensive effects in unanesthetized normotensive rats. The rats are prepared for measuring blood pressure directly from the aorta through a chronic indwelling cannula (Weeks and Jones, Proc. Soc. Exptl. Biol. and Med., 104, 646, 1960). Mean arterial pressure is measured prior to and at 4 hours and 24 hours after drug administration at a specified dose. The results in lowering blood pressure are set forth in the table below:

| Oral Dose mg./kg. | Rat No. | Initial B.P. mm Hg | B.P. Change mm Hg | |
|---|---|---|---|---|
| | | | 4 hr. | 24 hr. |
| 50 | 643 | 138 | −16 | −22 |
| | 646 | 134 | −22 | −28 |
| | 679 | 128 | − 6 | −16 |
| | 686 | 130 | − 8 | 0 |
| | avg | 133 | −13 | −17 |
| 25 | 669 | 142 | −22 | −22 |
| | 678 | 148 | −30 | −28 |
| | 627 | 130 | − 6 | −22 |
| | 638 | 132 | −12 | −20 |
| | avg | 138 | −18 | −23 |
| 12.5 | 651 | 132 | − 6 | −24 |
| | 652 | 128 | − 8 | − 6 |
| | 660 | 138 | − 8 | −24 |
| | 665 | 130 | − 4 | −12 |
| | avg | 132 | − 7 | −17 |
| 6.35 | 677 | 140 | −14 | −10 |
| | 696 | 140 | −14 | −14 |
| | 697 | 132 | − 8 | −10 |
| | 710 | 138 | −16 | −14 |
| | avg | 138 | −13 | −12 |
| 3.12 | 672 | 134 | −18 | −18 |
| | 676 | 128 | +12 | − 6 |
| | 680 | 130 | 0 | −10 |
| | 690 | 130 | + 2 | − 2 |
| | avg | 131 | − 1 | − 9 |
| 1 | 692 | 134 | 0 | − 4 |
| | 694 | 130 | − 8 | −10 |
| | 703 | 132 | + 2 | 0 |
| | 708 | 130 | 0 | + 2 |
| | avg | 132 | − 2 | − 3 |

EXAMPLE 20

Solid Preparation of Oral Administration

The essential active ingredient is suspended in a normal mouse diet to provide a concentration in the diet of from about 0.03 to about 0.3%. Groups of male mice, 18–22 gm. each, are fed a stock diet containing various concentrations of the essential active ingredient. Motor activity is determined after 20 hours on the diet, four groups of two mice from each test group being placed in actophotometers. After a ten minute acclimation period, motor activity is recorded for a ten minute period with the following results:

| % Conc. in Diet | 24 Hour Drug Intake mg./kg. | % Inhibition Motor Activity |
|---|---|---|
| 0.3 | 94 | 92 |
| 0.1 | 95 | 96 |
| 0.3 | 47 | 68 |

EXAMPLE 21

Ten thousand tablets for oral use, each containing 50 mg. of the essential active ingredient and 25 mg. melitracen, are prepared from the following ingredients and using the procedure of Example 14:

| | |
|---|---|
| Essential active ingredient micronized | 500 gm. |
| Melitracen, powdered | 250 gm. |
| Lactose | 1,000 gm. |
| Corn starch | 500 gm. |
| Talc | 500 gm. |
| Calcium stearate | 25 gm |

This tablet is useful in treating adult humans suffering from agitated depression by administering 1 tablet 3 times a day.

EXAMPLE 22

Ten thousand tablets for oral use, each containing 100 mg. of essential active ingredient and 320 mg. acetaminophen, are prepared from the following ingredients and using the procedure of Example 14:

| | |
|---|---|
| Essential active ingredient, finely powdered | 1,000 gm. |
| Acetaminophen, finely powdered | 3,200 gm. |
| Corn starch | 500 gm. |
| Talc | 500 gm. |
| Calcium stearate | 50 gm. |

This tablet is useful in treating pain and reducing agitation in an adult patient following surgery by administering one or two tablets 3 times a day depending on the severity of the condition.

EXAMPLE 23

Following the procedure of the preceding Examples 9 to 22, inclusive, similar dosage forms are prepared by substituting an equivalent amount of the other inventive compounds or their acid addition salts, such as:

1-[p-[[(7-trifluoromethyl)-4-quinolyl]amino]benzoyl]-piperazine dihydrochloride;
p-[(7-trifluoromethyl-4-quinolyl)amino]-N,N-pentamethylene benzamide hydrochloride;

p-[(7-trifluoromethyl-4-quinolyl)amino]-N,N-(3-oxapentamethylene)benzamide hydrochloride;

p-[(7-trifluoromethyl-4-quinolyl)amino]-N-methylbenzamide hydrochloride;

p-[(7-trifluoromethyl-4-quinolyl)amino]-N,N-dimethylbenzamide;

p-[(7-trifluoromethyl-4-quinolyl)-N-ethylamino]-N,N-(3-methyl-3-azapentamethylene)benzamide;

p-[(7-tribromoethyl-4-quinolyl)amino]-N,N-(3-methyl-3-azapentamethylene)benzamide;

p-[(7-trichloromethyl-4-quinolyl)amino]-N,N-(3-methyl-3-azapentamethylene)benzamide; and p-[(6-trifluoromethyl-4-quinolyl)amino]-N,N-(3-methyl-3-azapentamethylene)benzamide.

Although not necessary in the embodiments of the invention concept, additional active ingredients are incorporated in the present pharmaceutical dosage unit forms as desired. Each pharmaceutical dosage unit form contains therein an amount within the following nontoxic effective ranges: antihypertensive and diuretic agents such as reserpine (0.05 to 1 mg.), hydralazine (10 to 100 mg.), methyldopa (100 to 250 meg.), guanethidine (10 to 50 gm.), hydrochlorothiazide (15 to 50 mg.), and ethoxzolamide (50 to 150 mg.); tranquilizers, antipsychotic and anti-anxiety agents such as chlorpromazine (5 to 50 mg.), thioridazine (5 to 100 mg.), haloperidol (0.5 to 5 mg.), meprobamate (100 to 400 mg.), chlordiazepoxide (5 to 50 mg.), diazepam (2 to 15 mg.), and ectylurea (100 to 300 mg.); barbiturates such as phenobarbital (8 to 60 mg.), butabarbital (8 to 60 mg.), and amobarbital (16 to 120 mg.); analgesics such as aspirin (150 to 600 mg.) and acetaminophen (150 to 600 mg.); and antidepressants such as amitriptyline hydrochloride (10 to 50 mg.), methylphenidate hydrochloride (5 to 20 mg.), d-amphetamine sulfate (2 to 15 mg.), methamphetamie hydrochloride (2 to 15 mg.) and melitracen (15 to 50 mg.).

I claim:

1. p-[(7-trifluoromethyl-4-quinolyl)amino]-N,N-(3-methyl-3-azapentamethylene)benzamide.

2. 1-[p-[[(7-trifluoromethyl)-4-quinolyl]amino]benzoyl]piperazine dihydrochloride.

3. A pharmaceutical dosage unit form adapted to systemic administration to obtain anti-hypertensive and anti-anxiety effects consisting essentially of an effective non-toxic amount for said effects within the range of from about 10 mg. to about 1000 mg. of p-[(7-trifluoromethyl-4-quinolyl)amino]-N,N-(3-methyl-3-azapentamethylene)benzamide in combination with pharmaceutical means which adapt the compound for systemic administration.

4. A pharmaceutical dosage unit form adapted to systemic administration to obtain antihypertensive and anti-anxiety effects consisting essentially of an effective non-toxic amount for said effects within the range of from about 10 mg. to about 1000 mg. of 1-[p-[[(7-trifluoromethyl-4-quinolyl]amino]benzoyl]piperazine dihydrochloride in combination with pharmaceutical means which adapt the compound for systemic administration.

5. A method of obtaining antihypertensive and anti-anxiety effects in a mammal which consists essentially of administering systemically to the mammal a pharmaceutical dosage unit form supplying an effective non-toxic amount for antihypertensive and anti-anxiety effects of p-[(7-trifluoromethyl-4-quinolyl)amino]-N,N-(3-methyl-3-azapentamethylene)-benzamide or the pharmacologically acceptable acid addition salts thereof wherein the amount of compound administered is within the range of from about 0.1 mg. per kg. to about 15 mg. per kg. of weight of the mammal.

6. A method of obtaining antihypertensive and anti-anxiety effects in a mammal which consists essentially of administering systemically to the mammal a pharmaceutical dosage unit form supplying an effective non-toxic amount for antihypertensive and anti-anxiety effects of 1-[p-[[(7-trifluoromethyl)-4-quinolyl]amino]benzoyl]piperazine dihydrochloride wherein the amount of compound administered is within the range of from about 0.1 mg. per kg. to about 15 mg. per kg. of weight of the mammal.

* * * * *